United States Patent [19]

Allred et al.

[11] Patent Number: 5,803,905
[45] Date of Patent: Sep. 8, 1998

[54] SURGICAL CAMERA AND LIGHT ASSEMBLY ALLOWING ADJUSTABLE FOCUS AND ZOOM CAPABILITY AND METHOD OF USE

[75] Inventors: Jeff L. Allred, West Jordan; Oscar C. Johnson; Gene R. Oakes, both of Centerville; G. Lynn Rasmussen, Salt Lake City, all of Utah

[73] Assignee: Ajor Medical Technologies, L.L.C., Centerville, Utah

[21] Appl. No.: 623,589

[22] Filed: Mar. 28, 1996

[51] Int. Cl.⁶ .......................................................... A61B 1/06
[52] U.S. Cl. ............................................ 600/249; 362/804
[58] Field of Search ...................................... 600/249, 122, 600/167, 133; 362/804; 348/77, 373, 722; 396/12, 14, 200, 199

[56] References Cited

U.S. PATENT DOCUMENTS

| | | |
|---|---|---|
| 2,911,518 | 11/1959 | Anderson . |
| 3,360,647 | 12/1967 | Ernst-Otto Seitz et al. . |
| 3,891,842 | 6/1975 | Strusinski . |
| 4,384,315 | 5/1983 | Hayakawa . |
| 4,517,632 | 5/1985 | Roos . |
| 4,559,671 | 12/1985 | Andrews et al. . |
| 4,616,257 | 10/1986 | Kloots et al. . |
| 4,621,283 | 11/1986 | Feinbloom . |
| 4,639,838 | 1/1987 | Kato et al. ............................... 362/804 |
| 4,797,736 | 1/1989 | Kloots et al. . |
| 5,347,431 | 9/1994 | Blackwell et al. . |

OTHER PUBLICATIONS

Advertising Literature for a vividImage™ Video System, © 1992, vts.
Advertising Literature for a Sky–Eye®, Overhead Camera Systems, Inc., Wichita, Kansas.

Primary Examiner—John P. Leubecker
Attorney, Agent, or Firm—Kirton & McConkie; Berne S. Broadbent; Dale E. Hulse

[57] ABSTRACT

A surgical camera assembly and method for visually producing an operative field with enhanced focal illumination is disclosed as including a retaining assembly operably disposed in connection with a light source. Preferably, the retaining assembly provides a sterile surface for orienting the light source in relation to the operative field and includes a means for retaining a first end of camera lens. Removably disposed in operable engagement with the retaining assembly, the camera lens comprises an elongated body and a variable focus and zoom capability for producing visual images of the operative field. The elongated body of the camera lens is removably introduced within a channel formed in the body of a housing assembly. In preferred relationship, the housing assembly provides a sterile surface for manually adjusting the variable focus and zoom capability of the camera lens for purposes of enhancing the visual images of the operative field produced by the lens. In operation, a camera head converts the visual images produced by the camera lens into electrical signals. The electrical signals are transmitted by an electrical cable to a remote camera controller. The camera controller processes the electrical signals received from the camera head and converts these electrical signals into visual images for display on a display screen and provides means for recording the operative procedure.

39 Claims, 5 Drawing Sheets

SURGICAL CAMERA AND LIGHT ASSEMBLY ALLOWING ADJUSTABLE FOCUS AND ZOOM CAPABILITY AND METHOD OF USE

BACKGROUND

1. The Field of the Invention

This invention relates to camera mounting assemblies and, more particularly, to novel systems and methods for disposing a surgical camera assembly in connection with a light source to provide means for visually reproducing for demonstration an operative field with enhanced focal illumination and which is capable of providing a sterile surface for positioning the camera over the operative field and for manually adjusting the focus and zoom capability of the camera lens.

2. The Background Art

Traditionally, in an operating room, clinical laboratory, research facility, doctor's office or the like where operative procedures are typically performed in a sterile environment, only those persons fortunate enough to be in the immediate proximity of the operating table or seated in an adjoining amphitheater, if available, are capable of viewing the operative procedure as it progresses. Usually, only those observers permitted to stand at the surgeon's side or in a position adjacent the operating table receive the full visual benefit of the operative techniques performed by the surgeon.

It is often impossible for persons to observe an operative procedure when situated in the immediate proximity of the operating table without physically disrupting the movements of the surgeon and/or his assistants and, more importantly, without disturbing the sterile field or environment religiously maintained in the operating room to avoid potential patient contamination or infection. In light of the foregoing, the viewing of a surgical procedure would seem to be best conducted at a location remote from the operating table in order to avoid interfering with the surgeon and surgical assistants and to further circumvent disturbing the maintenance of a sterile surgical environment.

Because it has recently become more and more important that the visual images of an operative field be made available for observation and study by other physicians, surgical assistants, and/or medical students as a form of instruction or teaching aid, especially when dealing with atypical cases, systems and methods have been developed by those skilled in the art which provide means of reproducing the images of an operative field for demonstration to an audience which is not necessarily limited by the size of the operating room or adjacent amphitheater. Moreover, in light of a seemingly litigious society, not only can the reproduction of a surgical procedure be used for instructional purposes, but also for the purpose of preserving a record of the procedure for use in a possible malpractice suit or the like.

As explained above, to avoid the disadvantages associated with disturbing the activity of a surgeon and the surgical assistants or interfering with the preservation of a sterile environment, prior art methods and camera assemblies were conceived in an attempt to alleviate the foregoing intrusions. For example, prior art surgical camera assemblies were developed by those skilled in the art comprising a camera disposed in connection with an articulating extension arm or boom assembly providing means for positioning the camera over the operating table in order to allow for still photography or remote viewing of the operative procedure.

The benefits of prior art surgical camera assemblies disposed in connection with boom or support assemblies of the prior art are typically limited in functionality by their inherent inability to enter the sterile field thus restricting the potential views available of the operative field for visual reproduction. Similarly, a surgical procedure performed within a small internal cavity of the body may not be visually reproducible by a camera mounted on a boom or support assembly, especially if the suspended camera is not in a position directly over the particular operative location of the surgical intervention (i.e., retained along side the operating table or suspended overhead the illumination lamps). At best, the surgical site may appear along the periphery of the area being viewed, and not in the center of the operative location to provide a clear and unobstructed reproduction of the operative procedure. Moreover, while individuals may be able to view only a portion of the operative procedure, they generally are unable to visualize the operating site in the same manner and from the same view as the surgeon. In addition, prior art camera assemblies of this type are generally operated remotely by one or more technical operators who are responsible for manually manipulating the necessary controls in order to orient the camera and adjust its focus and zoom capability, if available, as is usually performed under the verbal supervision of the attending surgeon.

To alleviate the various disadvantages associated with prior art surgical cameras disposed in connection with boom or support assemblies, those skilled in the art developed surgical camera assemblies comprising a light source and a horizontally mounted camera both being suitably supported from the ceiling of an operating room and including a reflecting element (e.g., a mirror). The reflecting element is operably mounted above the light source and operating table so that an optical path can be provided from the table through an opening formed in the light source to the mirror and then by reflection to the particular camera lens used for recording the procedure. As technology further progressed, prior art surgical camera assemblies were developed by those skilled in the art incorporating a handle member fixed in relation to a surgical lamp, whereby the handle member provides means for housing a television camera and lens directed in such a manner so that the focal axis of the lens is substantially co-linear with the focal axis of the lamp.

The advantage of prior art surgical camera assemblies operatively disposed in connection with a light source are typically contingent upon the ability to direct the light source in such a manner so as to acquire the maximum effect of illumination while simultaneously directing the lens of the camera in precisely the same direction, whereby, in combination, attempting to facilitate optimum still photography or video imaging without interfering with the illumination of the operative field. Although prior art surgical camera assemblies engaging a high intensity light source generally afford meaningful advantages over the use of still photography or video cameras disposed in connection with boom or support assemblies, the overall effectiveness of such prior art surgical camera assemblies has been frequently questioned in view of providing adequate and efficient means by which to adjust or direct the illumination provided by the light source and orient the visual field of the camera lens.

As noted above, at least one high intensity light is typically disposed in an operating room to provide adequate illumination on an operating room table in order to perform surgical procedures. During the normal course of an operation, the light source may be directed and redirected by the non-sterile operating room staff in response to the directions voiced by the operating surgeon or surgical assistants. As with the direction of the light source, prior art surgical camera assemblies are usually manipulated by operating room staff or remote operators who are also verbally instructed as to the exact location where the surgeon desires the still or video images to be taken.

Because many surgeons prefer to adjust the lighting and camera assembly personally so that the precise location to be illuminated and visual images to be reproduced can be quickly and easily obtained, those skilled in the art developed surgical camera assemblies consisting of a handle member providing a sterile surface and being operatively disposed in connection with a light source. In structural design, a camera and lens are integrally disposed within the body of the sterile handle member, thus providing the surgeon or surgical assistants with a sterile surface for personally orienting the lighting and the camera assembly rather than having to verbally direct the operating room staff or a remote operator in the adjustment processes.

Unfortunately, however, prior art surgical camera assemblies having a camera and lens disposed within a sterile handle member of the type discussed above, generally require the custom installation of a hard-wired camera system and a lens comprising a fixed focal length. In this regard, the camera disposed within the sterile handle member is generally dedicated to a single operating room and the fixed focal length of the lens provides no means of adjustment in relation to varying a focus or zoom capability.

As illustrated by the number of prior art patents and other disclosures, efforts are continuously being made in an attempt to remedy the foregoing disadvantages. These and other difficulties coupled with the visual difficulties and limitations of prior art surgical camera assemblies have been addressed in a novel manner by the present invention.

BRIEF SUMMARY AND OBJECTS OF THE INVENTION

In view of the foregoing, it is a primary object of the present invention to provide a surgical camera assembly disposed in connection with a light source to provide means for visually reproducing for demonstration a "bird's eye" view of an operative field with enhanced focal illumination and without disrupting the focal field of the surgical light by means of shadowing, whereby observers are provided with a clear and unobstructed view of the surgical procedure as it progresses.

It is also an object of the present invention to provide a surgical camera assembly and method for visually reproducing an operative field with enhanced focal illumination which incorporates a retaining assembly providing a sterile surface for orienting the light source and camera assembly in relation to the operative field and which is capable of providing means for being universally interchangeable or adaptable to various lighting systems or surgical lamps found in the offices of physicians, clinical laboratories, research facilities, emergency rooms, dentist offices or the like.

Further, it is an object of the present invention to provide a surgical camera assembly and method for visually reproducing an operative field with enhanced focal illumination which comprises a lens cover for housing a camera lens, the housing assembly providing a sterile surface for adjusting the variable focus and zoom capability of the lens.

Similarly, it is an object of the present invention to provide a surgical camera assembly and method for visually reproducing an operative field with enhanced focal illumination which is capable of providing means for increasing or decreasing the magnification of the images produced by the camera lens without having to physically move the light source in and out of the operative field.

It is a still further object of the present invention to provide a surgical camera assembly and method for visually reproducing an operative field with enhanced focal illumination which incorporates a camera assembly that is readily adaptable and removable as an enhancement to existing equipment or systems, whereby avoiding the costs of installation associated with hard-wiring a dedicated camera to a single light source.

Additionally, it is an object of the present invention to provide a surgical camera assembly and method for visually reproducing an operative field with enhanced focal illumination which comprises a housing assembly adaptable for pre-sterilization and for packaging as a disposable product, thus being generally cost effective in light of mass production and readily available for an emergency procedure.

Consistent with the foregoing objects, and in accordance with the invention as embodied and broadly described herein, a surgical camera assembly and method for visually reproducing an operative field with enhanced focal illumination is disclosed in one presently preferred embodiment of the present invention as including a retaining assembly operably disposed in connection with a light source. Preferably, the retaining assembly provides a sterile surface for orienting the light source in relation to the operative field and includes a means for retaining a first end of a camera lens. Removably disposed in operable engagement with the retaining assembly, the camera lens comprises an elongated body and a variable focus and zoom capability for producing visual images of the operative field. The elongated body of the camera lens is removably introduced within a channel formed in the body of a lens cover or housing assembly. In preferred relationship, the housing assembly provides a sterile surface for manually adjusting the variable focus and zoom capability of the camera lens to provide means for enhancing the visual images of the operative field produced by the lens. In operation, a camera head converts the visual images produced by the camera lens into electrical signals. The electrical signals are preferably transmitted by an electrical cable to a remote camera controller. The camera controller processes the electrical signals received from the camera head and converts the electrical signals into visual images for display on a display screen and may further provide means for recording the operative procedure.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the system and methods of the present invention, as represented in FIGS. 1 through 7, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

Figure 1:
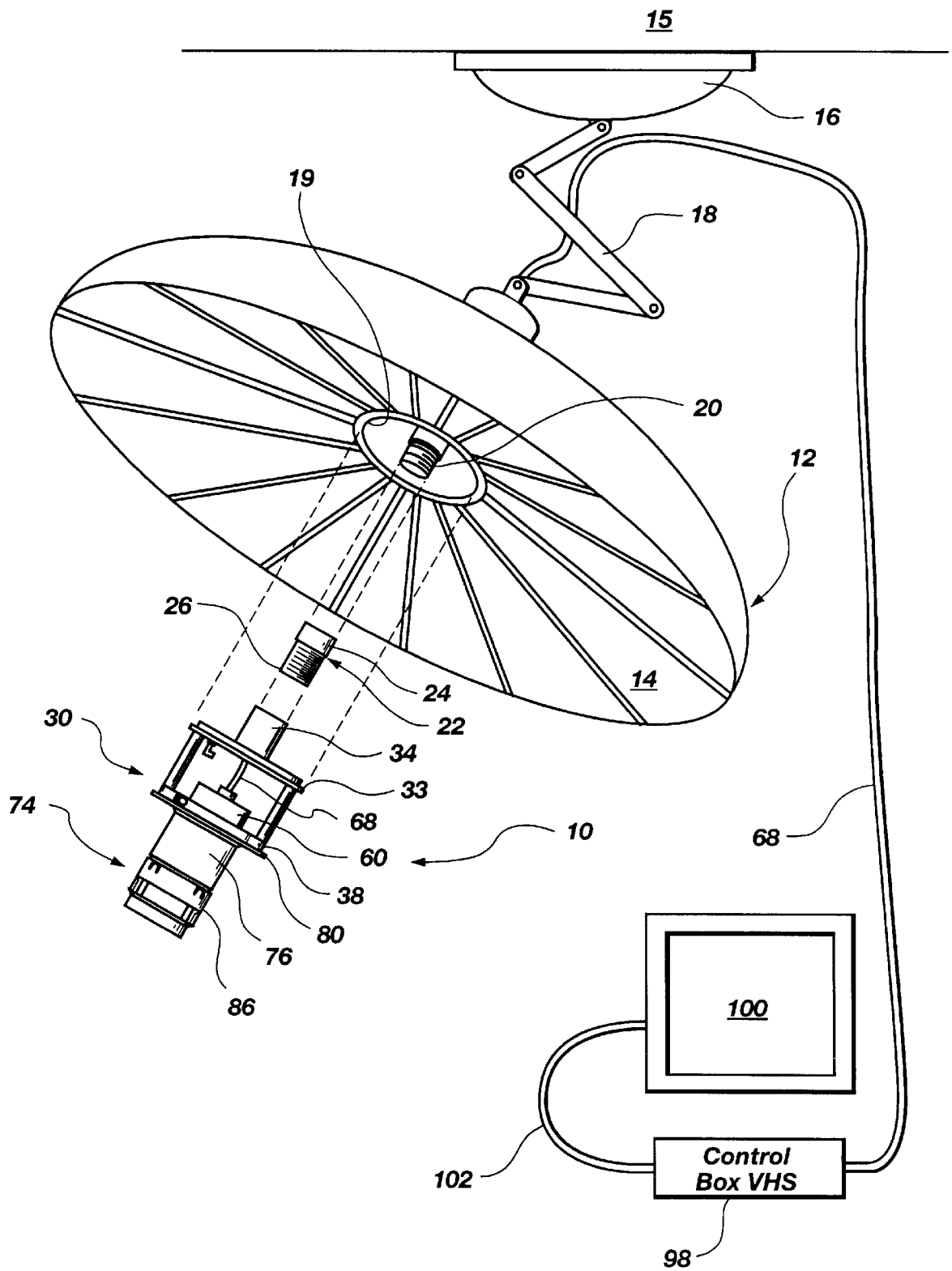
FIG. 1 is a perspective view of a surgical camera assembly of one presently preferred embodiment of the present invention being disposed in operable engagement with a light source supported by a support structure in accordance with one presently preferred embodiment of the present invention.
Figure 5:
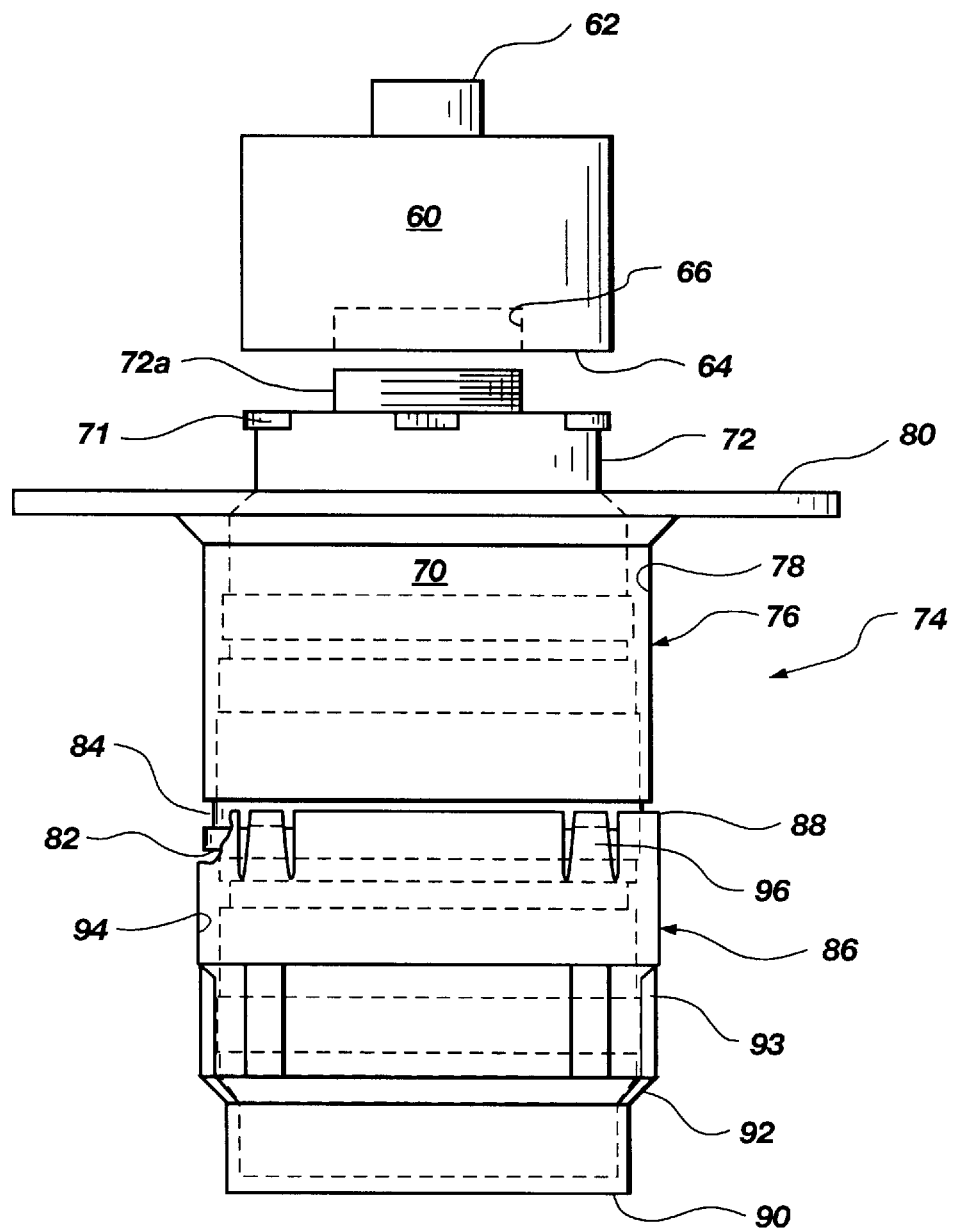
FIG. 5 is an exploded perspective view of a housing assembly of one presently preferred embodiment of the present invention housing an optical lens therein.

One presently preferred embodiment of the surgical camera assembly of the present invention, designated generally at 10, is illustrated in FIG. 1. As shown, the surgical camera assembly 10 comprises a retaining assembly 30 disposed in alignment with an intermediate connecting member 22 further disposed in alignment with a conventional light source 12. Engaging an opposing end of the retaining assembly 30 is a sterile lens cover 74 having an internal channel for removably housing a camera lens 70 therein, as best shown in FIG. 5.

In one presently preferred embodiment of the present invention, the light source 12 incorporates a conventional high intensity light. The light source 12 may be formed having an internal facing 14 comprising a reflective surface which provides enhanced light reflection for illuminating an operative field. As illustrated in FIG. 1, the light source 12 is preferably suspended from a support structure including a support member 16 and at least one articulating extension arm 18 pivotally connected between the light source 12 and the support member 16. In present construction, the support member 16 is rigidly mounted at the ceiling 15 of an operating room. Additionally, the light source 12 is pivotally disposed about numerous axles by means of several articulating extension arms 18 extending from the support member 16 in such a manner that the light source 12 can be manually directed and redirected into a plurality of positions, both horizontally and vertically, for optimum illumination of the operative field.

Alternately, the light source 12 may be pivotally disposed in connection with one or more articulating extension arms 18 extending from a portable support member 16 mounted at the ceiling 15 of the operating room and further engaging an elongated support track. The support track is preferably formed having a predetermined length and providing means for slidably moving the support member 16 along the periphery of the support track. In design, the support track may be formed having virtually any configuration or shape such as, for example, being partially or completely circular and/or linear or the support track may have a portion which is operably suspended from the ceiling 15. In addition to the foregoing means for supporting a light source, those skilled in the art will readily recognize other possible modifications and adaptations which are consistent with the spirit and scope of the present invention.

Projecting substantially outward from a radially enlarged opening 19 centrally formed in the facing 14 of the light source 12 is a conventional attachment member 20. In one presently preferred embodiment of the present invention, the attachment member 20 is formed having a generally cylindrical configuration and including a plurality of interlocking threads or ribs disposed at a first end on the external surface thereof.

As best shown in FIG. 1, the intermediate connecting member 22 is preferably formed having a generally cylindrical configuration and operably disposed in alignment between the attachment member 20 of the light source 12 and the retaining assembly 30 of the camera assembly 10. A first end 24 of the intermediate connecting member 22 is preferably formed having an internal diameter appropriately sized for engagement with the interlocking threads or ribs of the attachment member 20. Disposed within the internal diameter of the first end 24 of the intermediate member 22 is a plurality of interlocking threads or ribs which may correspondingly engage the threads or ribs of the attachment member 20 when rotatably introduced thereover to form a connection therebetween. It will be readily appreciated by those skilled in the art, however, that other suitable means for connecting the retaining assembly 30 to the light source 12 are possible. For example, other conventional fastening or connecting means, such as, for example, a snap-fit engagement, a frictional engagement, etc. which are consistent with the spirit and scope of the present invention are possible.

An alternate embodiment of the present invention may comprise an operative engagement between the retaining assembly 30 of the camera assembly 10 and the attachment member 20 of the light source 12 without disposing the intermediate connecting member 22 therebetween. In function, however, the use of the intermediate member 22, as disclosed in the presently preferred embodiment, provides means for facilitating a form of universal adaptability or interchangeability to various lighting systems or surgical lamps, thus providing means for enhancing existing equipment or systems for purposes of readily accommodating the engagement of the surgical camera assembly 10 of the present invention.

Figure 2:
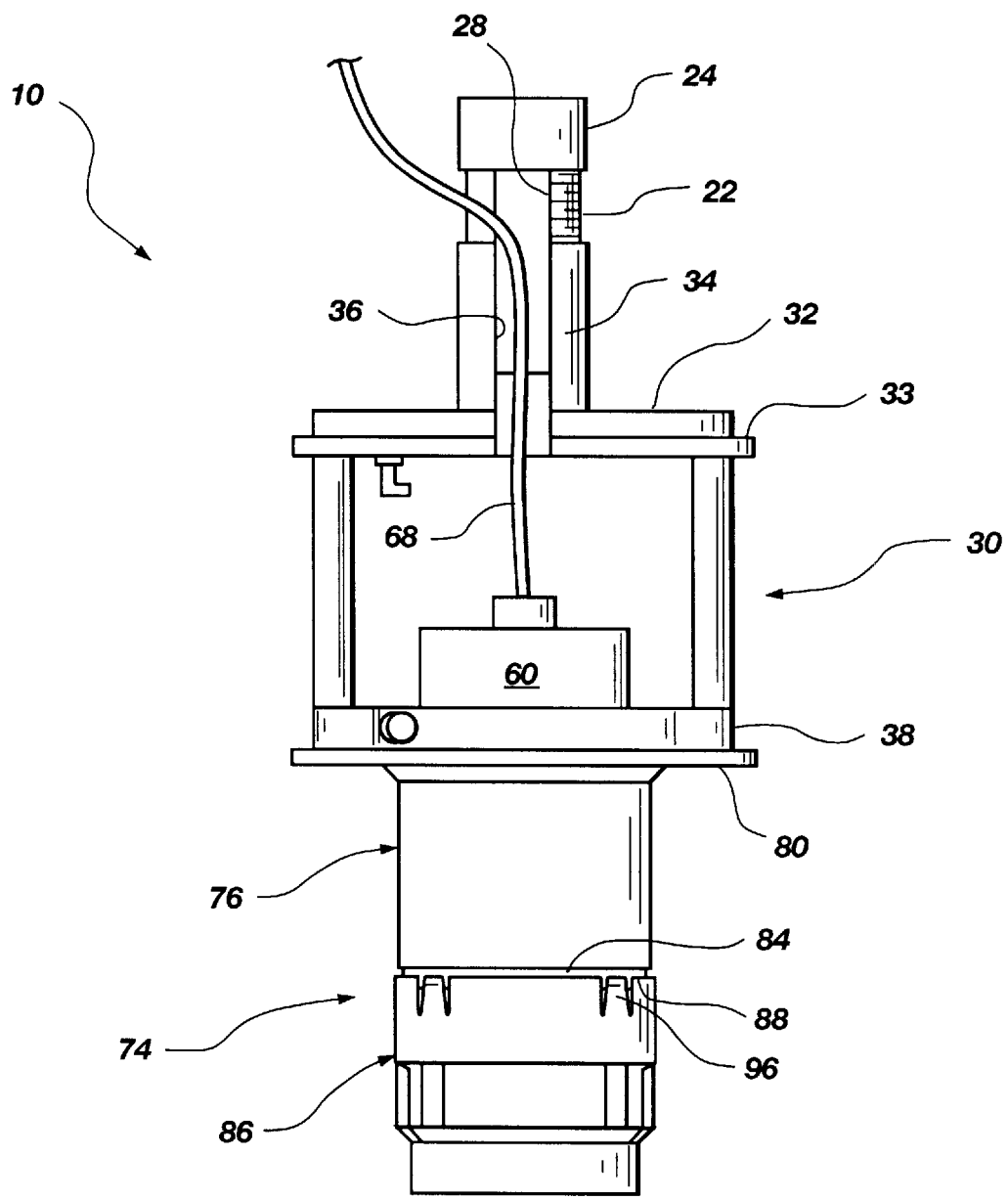
FIG. 2 is a perspective view of the surgical camera assembly of one presently preferred embodiment of the present invention as shown in FIG. 1.
Figure 3:
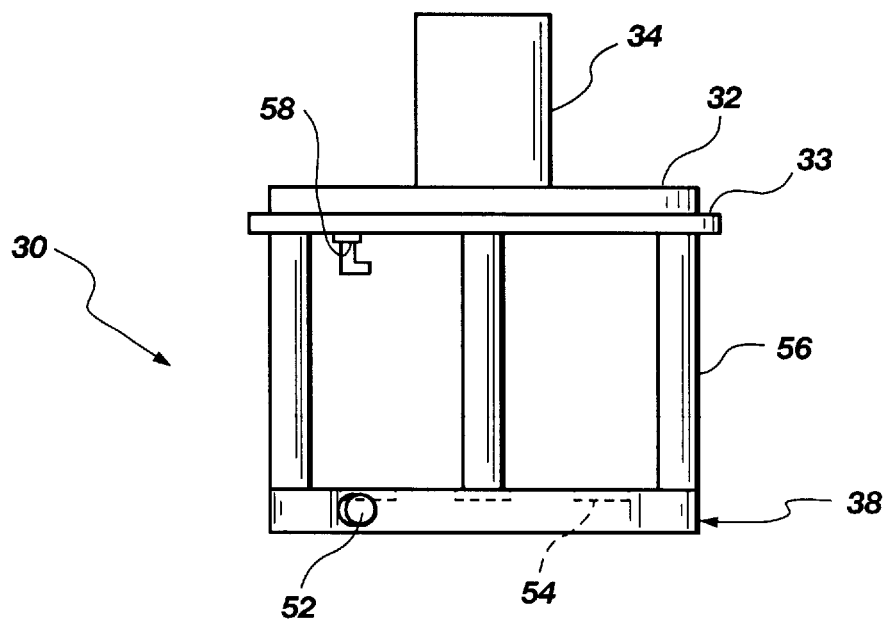
FIG. 3 is a perspective view of a retaining assembly of one presently preferred embodiment of the present invention.
Figure 4:
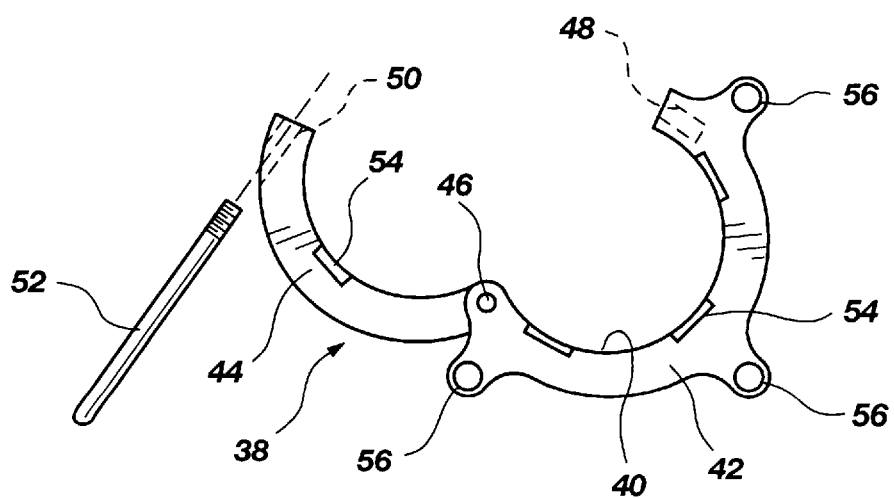
FIG. 4 is an elevational view of the second end of the retaining assembly of one presently preferred embodiment of the present invention as shown in FIG. 3.

Referring now to FIGS. 2, 3 and 4, the retaining assembly 30 is formed of a substantially rigid material which is preferably capable of being sterilized in order to provide a sterile surface for manually orienting the light source 12 and the camera lens 70 when disposed in engagement therewith. In one presently preferred embodiment of the surgical camera assembly 10, the retaining assembly 30 is formed of Aluminum T6. It will be readily appreciated, however, that other suitable materials are possible. For example, the retaining assembly 30 may be formed of other suitable metals or alloys, ceramic (of or relating to any product as earthen-ware, porcelain, brick, glass, vitreous enamels, etc.), fiberglass, any of numerous organic, synthetic or processed materials which are mostly thermoplastic or thermosetting polymers of high molecular weight, with or without additives, such as, plasticizers, auto oxidants, colorants, or fillers, and which can be shaped, molded, cast, extruded, drawn, foamed or laminated into objects, films or filaments, or any other suitable composite material readily known in the art to be substantially rigid.

In structure, the retaining assembly 30 is formed having a first end 32 and a second opposing end 38. In one presently preferred embodiment of the retaining assembly 30, the first end 32 of the retaining assembly 30 may be formed comprising a radially enlarged flange 33 disposed in rotatable connection therewith and having a diameter substantially complimentary to the diameter of the opening 19 formed in the facing 14 of the light source 12. In preferred function, the radially enlarged flange 33 may provide means for shielding the sterile hand of a surgeon or surgical assistant from the non-sterile surface of the light source 12 when orienting the light source 12 and camera assembly 10 over the operative field. It will be readily appreciated by those skilled in the art, however, that other shapes or configurations of the first end 32 and flange 33 are possible.

Extending between the flange 33 and the second opposing end 38 of the retaining assembly 30 is at least one gripping member 56 disposed in rigid connection therebetween, as identified in FIG. 3. In the presently preferred embodiment of the present invention, one or more gripping members 56 are provided to further assist the surgeon or surgical assistants in manually orienting the light source 12 and the camera assembly 10 over the operative field for an unobstructed and clean view of the surgical procedure.

Disposed at the second opposing end 38 of the retaining assembly 30 is an openable orifice 40, as best shown in FIG. 4. In preferred design, the orifice 40 is formed having a substantially circular configuration and including an internal periphery sufficient in diameter to allow for the introduction of a first end 72 of the camera lens 70, as disclosed by reference to FIG. 5. It will be readily appreciated by those skilled in the art, however, that other shapes or configurations of the orifice 40 are possible such that the internal periphery of the orifice 40 is sufficient in size and dimension to allow for the introduction of the first end 72 of the camera lens 70.

Referring back to FIG. 4, the orifice 40 at the second end 38 of the retaining assembly 30 preferably comprises a stationary member 42 and a pivotal swing arm assembly 44. The stationary member 42 may be fixed in relation to the retaining assembly 30 by means of at least one gripping member 56 disposed in connection therewith. Correspondingly, the swing arm assembly 44 may be fixed in relation to the stationary member 42 by means of a pivotal arrangement 46, such as, for example, a pivot pin. The pivotal arrangement 46 disposed in operative engagement between the stationary member 42 and the swing arm assembly 44 is preferably fixed in relation therebetween to provide means for opening or closing the orifice 40. Similarly, the stationary member 42 and the swing arm assembly 44 provide means for forming a restriction collar by means of introducing a fastener 52 through a through-bore 50 formed in the pivotal swing arm assembly 44 at an end opposite the end providing a pivotal connection with the stationary member 42 and further introducing the fastener 52 into a corresponding through-bore 48 formed in the stationary member 42 at an end opposite the end providing the pivotal connection with the swing arm assembly 44. Preferably, the fastener 52 comprises a clamp screw, bolt, rivet, or other suitable fastening means.

In operation, the swing arm assembly 44 is removably released from its fixed engagement with the stationary member 42 to provide means for opening the orifice 40 in order to removably introduce the first end 72 of the camera lens 70 within the internal periphery of the orifice 40. In preferred construction, at least one alignment member 54 is formed in the upper surface of the stationary member 42 or swing arm assembly 44 (see FIGS. 3 and 4) to provide means for securing the first end 72 of the camera assembly 70 in relation to the second end 38 of the retaining assembly 30. Preferably, a plurality of alignment members 54 are formed in the stationary member 42 and swing arm assembly 44 which operably engage corresponding alignment tabs 71 disposed in the first end 72 of the camera lens 70, as illustrated in FIG. 5.

Referring now to FIGS. 2 and 5, operably disposed in engagement with a connecting member 72a formed at the first end 72 of the camera lens 70 is a suitable camera head 60. Preferably, the camera head 60 is formed having a generally cylindrical shape and comprising an opening 66 disposed at a second end 64 thereof. The opening 66 at the second end 64 of the camera head 60 is formed having an appropriately sized internal periphery being sufficient in size to receive the connecting member 72a of the camera lens 70. Further, the opening 66 of the camera head 60 comprises a plurality of interlocking threads or ribs integrally formed within its internal periphery to provide means for engaging a plurality of interlocking threads or ribs disposed on the external surface of the connecting member 72a. Removably introduced within the internal periphery of the opening 66 at the second end 64 of the camera head 60, the threaded portion of the connecting member 72a of the camera lens 70 correspondingly engages the threaded portion of the opening 66 of the camera head 60 when rotatably introduced therein. As will be readily appreciated by those skilled in the art, however, other suitable means for connecting the camera head 60 to the camera lens 70 are possible, such as, for example, a snap-fit engagement, a frictional engagement, etc.

In one presently preferred embodiment of the present invention, the camera head 60 and power source may comprise a Panasonic® 3-CCD micro head color video camera incorporating digital signal processing technology, Part No. GP-US502, having the following specifications as identified in the table below:

| | | |
|---|---|---|
| PICK-UP SYSTEM | | Micro Prism System (F1.0) |
| IMAGE SENSOR | | Three ½" interline transfer |
| | | (IT) High sensitivity CCDs |
| PIXELS | (NTSC) | 768 (H) × 494 (V) pixels |
| | (PAL) | 752 (H) × 582 (V) pixels |

| | | |
|---|---|---|
| SCANNING STANDARD | (NTSC) | 525 lines, 60 fields, 30 frames; Horizontal: 15.734 kHz Vertical: 59.94 Hz |
| | (PAL) | 625 lines, 50 fields, 25 frames Horizontal: 15.825 kHz; Vertical: 50.0 Hz |
| SYNCHRONIZING SYSTEM | (NTSC) | Internal or External (gen-lock), automatically switchable |
| | (PAL) | External (Gen-lock) Input: VBS/VS/HD/VD selectable |
| VIDEO OUTPUTS | (NTSC) | Video Output: BNC connector X2 1.0 Vp-p NTSC composite/75Q Y/C (S-video) Output: S-video connector X1 1.0 Vp-p (Y)/75Q RGB/SYNC Output: D-SUB 9-pin connector X1 R/G/B: 0.7 Vp-p each/75Q SYNC: 4 Vp-p/75Q or 0.3 Vp-p/75Q selectable VIDEO: NTSC composite/75Q |
| | (PAL) | Video Output: BNC connector X2 1.0 Vp-p PAL composite/75Q Y/C (S-video) Output: S-video connector X1 1.0 Vp-p (Y)/75Q 0.3 Vp-p Burst level (C)/75Q RCB/SYNC Output: D-SUB 9-pin connector X1 R/G/B: 0.7 Vp-p Each 75Q SYNC: 4 Vp-p/75Q or 0.3 Vp-p/75Q selectable VIDEO: PAL composite/75Q |
| REQUIRED ILLUMINATION | | 200 fc (2000 1x) at F8.0 3200"K |
| MINIMUM ILLUMINATION | | 0.9 fc (0 1x) at F2.8 with 18 dB gain, 30 IRE level (30% Output level) |
| SIGNAL-TO-NOISE RATIO | (NTSC) | 56 dB (Typical, luminance) without aperture and gamma |
| | (PAL) | 56 dB (Typical, luminance) without aperture and gamma |
| HORIZONTAL RESOLUTION | | 700 lines at center (Y signal) |
| WHITE BALANCE | | ATW (Automatic Tracing White Balance) AWC (Automatic White Balance Control) and Manual Control |
| BLACK BALANCE | | ABC (Automatic Black Balance) and Manual Control |
| COLOR BAR | | Built-in full color bar |
| ELECTRONIC SHUTTER | (NTSC) | Auto-Adjustable Step: 1/100 s, 1/250 s, 1/500 s, 1/1000 s 1/2000 s, 1/4000 s and 1/10000 s. Synchro Scan (Manual); 1/525–254/525 line |
| | (PAL) | Auto: Adjustable Step: 1/120 s, 1/250 s, 1/500 s, 1/1000 s 1/2000 s, 1/4000 s and 1/10000 s. Synchro Scan (Manual); 1/625–305/625 line |
| GAIN SELECTION | | AGC and Gain Up (Selectable) |
| SWITCHES | | Power On/Off (Power) Camera/Color Bar Selection (CAM/BAR) Gain Up Selection (OFF/LOW/HIGH (0/+9/+18 dB) Auto White/Auto Black Selection ATW/AWC/MANU Selection ELC (Electronic Light Control) On/Off.Page.item < (left) > (right) |
| CONTROLS | | R Gain, B Gain, ELC level |
| LENS MOUNT | | C-Mount |
| POWER SOURCE | | 12 V DC |
| POWER CONSUMPTION | | 0.4 W |
| AMBIENT OPERATING TEMPERATURE | | 32° F.–113° F. (0° C.–45° C.) |
| AMBIENT OPERATING HUMIDITY | | 30%–90% |

-continued

| DIMENSIONS | Camera Head: 1-⅝" (W) X1-¾" (H) X2" (D) (34 (W) X44 (H) X51.5 (D) mm) Camera Control Unit: 8-⅛" (W) X1-¾" (H) X9-½" (D) (206.5 (W) X44 (H) X250 (D) mm) |
|---|---|
| WEIGHTS | Camera Head: 0.24 lbs (0.11 kg) Camera Central Unit: 3.74 lbs (1.7 kg) |

It will be readily appreciated, however, that the foregoing illustration is merely representative of one presently preferred embodiment of the camera head and is not intended to be restrictive in relation to other suitable camera heads which may be utilized by the present invention as will be readily recognized by those skilled in the art.

Referring to FIGS. 1, 2 and 5, disposed at a first end 62 of the camera head 60 is an electrical connection providing means for connecting a camera cable 68. Preferably, the camera cable 68 provides an electrical connection between the camera head 60 and a camera controller 98 remotely positioned within the operating room. For the purpose of alleviating the camera cable 68 from being "under foot" in the operating room and in order to insure the maintenance of a sterile environment, the camera cable 68 is preferably disposed from the connection at the first end 62 of the camera head 60 through an elongated slot 36 formed in the base member 34 of the retaining assembly 30 and further introduced into an elongated channel 28 formed in the second end 26 of the intermediate connecting member 22 disposed in alignment with the elongated slot 36, as best shown in FIG. 2. Preferably extending from elongated channel 28 of the intermediate member 22, the camera cable 68 may be disposed adjacent the articulating extension arms 18 of the support member 16 and passed along the ceiling 15 of the operating room and finally disposed in connection with the remote camera controller 98.

By means of a preferred structural relationship, the elongated channel 28 of the intermediate connecting member 22 and the elongated slot 36 formed in the base member 34 of the retaining assembly 30 are preferably disposed in rotatable alignment with each other to provide means for retaining the camera cable 68 therein. In this regard, when the elongated channel 28 and the elongated slot 36 are rotatably disposed out of alignment therebetween, the portion of the camera cable 68 introduced therein is restricted from movement in relation to the sterile surface provided by the retaining assembly 30 of the surgical camera assembly 10.

As further disclosed in FIG. 5, the camera lens 70 is shown by broken lines for the purpose of illustrating its relationship with the lens cover 74 when housed therein. As noted above, the camera lens 70 comprises a first end 72 removably engaging the second end 38 of the retaining assembly, an elongated body disposed within the sterile lens cover 74, and a variable focus and zoom capability.

In one presently preferred embodiment of the present invention, the camera lens 70 may incorporate a Cannon® J6x11-II lens for ⅔" and ½" cameras comprising the following specifications as identified in the table below:

| FOCAL LENGTH | 11.5–69 mm |
|---|---|
| MAXIMUM RELATIVE APERTURE | 1:1.4 |
| IRIS | 1.4, 2.8, 5.6, 11, 22 Close |
| ZOOM RATIO | 6x |

-continued

| ANGULAR FIELD OF VIEW | ⅔" | 41.9' × 32' at 11.5 mm |
|---|---|---|
| | | 7.3' × 5.5' at 69 mm |
| | ½" | 31.1' × 23.6' at 11.5 mm |
| | | 5.3' × 4' at 69 mm |
| MINIMUM OBJECT DISTANCE | | 1.0 m (from front Vertex) |
| BACK FOCAL DISTANCE | | 17.93 mm |
| OPERATION SYSTEM | Zoom | Manual |
| | | Angle of Rotation 110° |
| | Focus | Manual |
| | | Angle of Rotation 140° |
| | Iris | Manual |
| | | Angle of Rotation 95° |
| FRONT THREAD | | 46 mm PO.75 |
| SIZE | | 58 × 97.3 mm |
| WEIGHT | | .41 kg |
| MOUNT | | C - Mount |
| ACCESSORY | | Ext. 2xA - 3/2xA - 2 |

It will be readily appreciated, however, that the foregoing illustration is merely representative of one presently preferred embodiment of the camera lens and is not intended to be restrictive in relation to other suitable lens which may be utilized by the present invention as will be readily recognized by those skilled in the art.

Disposed over a substantial portion of the elongated body of the camera lens 70 is a lens cover 74, as best illustrated in FIG. 5. In one presently preferred embodiment of the present invention, the lens cover 74 comprises an upper housing member 76 and an end piece 92. The upper housing member 76 is preferably formed of a substantially rigid material which is preferably capable of being sterilized in order to provide a sterile surface for assisting in the manual adjustment of the variable focus and zoom capability of the camera lens 70 when housed therein. Preferably, the upper housing member 76 is formed of Aluminum T6. It will be readily appreciated, however, that other suitable materials are possible. For example, the upper housing member 76 may be formed of other suitable metals or alloys, ceramic (of or relating to any product as earthen-ware, porcelain, brick, glass, vitreous enamels, etc.), fiberglass, any of numerous organic, synthetic or processed materials which are mostly thermoplastic or thermosetting polymers of high molecular weight, with or without additives, such as, plasticizers, auto oxidants, colorants, or fillers, and which can be shaped, molded, cast, extruded, drawn, foamed or laminated into objects, films or filaments, or any other suitable composite material readily known in the art to be substantially rigid.

In preferred structure, the upper housing member 76 is formed having a first end 80 and a second opposing end 82. The first end 80 of the housing member 76 may be formed having a radially enlarged rim comprising a peripheral surface area substantially complimentary in size to the diameter of the flange 33 formed at the first end 32 of the retaining assembly 30. In operation, the radially enlarged rim provides means for shielding the sterile hand of an operating room technician or surgical assistant from the non-sterile surface of the camera head 60 when disposing the connecting member 72a of the camera lens 70 in operable engagement with the camera head 60, as will be discussed in more detail below.

Formed between the first end 80 and the second opposing end 82 of the housing member 76 is a generally cylindrical channel 78 having an internal periphery sufficient in diameter for introducing the first end 72 and an upper portion of the elongated body of the camera lens 70 therein and further providing means for retaining the lens 70 in operative engagement therewith. It will be appreciated by those skilled in the art, however, that other shapes or configurations of the internal channel 78 are readily possible such that the internal periphery is sufficient in size and dimension to allow for the introduction and retention of the first end 72 and upper portion of the body of the camera lens 70.

In one presently preferred embodiment of the present invention, the end piece 86 of the lens cover 74 is formed having a generally cylindrical configuration and consisting of a substantially rigid polymeric material capable of being sterilized in order to provide a sterile surface for manually adjusting the variable focus and zoom capability of the camera lens 70 when disposed therein. Preferably, the end piece 86 is formed of a material which is inherently clear in color. Additionally, the end piece 86 may be formed of a material which is disposable in nature.

Consistent with the foregoing, one presently preferred embodiment of the present invention comprises an end piece 86 formed of a plexiglas SG-7 gamma resistant high flow impact modified acrylic molding resin having the ability to provide and maintain exceptional clarity after five megarads of gamma radiation without adverse effects on its physical properties including, such as, for example, biocompatibility, chemical resistance, and excellent moldability. It will be readily appreciated, however, that other suitable materials comprising the end piece 86 are possible, such as, for example, a metal or alloy, fiberglass, ceramic (of or relating to any product as earthen-ware, porcelain, brick, glass, vitreous enamels, etc.), any of numerous organic, synthetic or processed materials which are mostly thermoplastic or thermosetting polymers of high molecular weight, with or without additives, such as, plasticizers, auto oxidants, colorants, or fillers, and which can be shaped, molded, cast, extruded, drawn, foamed or laminated into objects, films or filaments, or any other composite material readily known in the art to be substantially rigid and capable of sterilization.

Disposed from a first end 88 of the end piece 86 is an elongated channel 94 having an internal periphery sufficient in diameter for introducing the lower body portion of the camera lens 70 therein and further providing means for retaining the lens 70 in operative engagement therewith. It will be readily appreciated by those skilled in the art, however, that other configurations or shapes of the elongated channel 94 are possible such that the internal periphery is sufficient in size and dimension to allow for the introduction and retention of the lower body of the camera lens 70.

In preferred design, the elongated channel 94 of the end piece 86 includes a substantially circular opening formed at the first end 88 thereof. Because the elongated channel 94 of one presently preferred embodiment of the present invention may be closed at the second end 90 of the end piece 86, the end piece 86 is preferably constructed of a substantially transparent material to provide means for allowing the camera lens 70 to readily produce images of the operative field therethrough. In contrast, an alternate preferred embodiment of the end piece 86 of the present invention may consist of a non-transparent, sterilizable material, whereby the elongated channel 94 formed therein may include an opening formed at the first end 88 and also at the second opposing end 90 of the end piece 86 to avoid obstructing the field of view of the camera lens 70. It will be readily appreciated by those skilled in the art from the foregoing description, that the end piece 86 may be substantially formed of a non-transparent material which comprises the second end 90 of the end piece 86 which is preferably formed of a transparent material, thus the field of view of the camera lens 10 is not obstructed.

Upon introduction of the camera lens 70 through the first end 88 of the end piece 86, the distal end of the camera lens 70 may rest against the second end 90 of the end piece 86. Preferably, the second end 90 of the end piece 86 is configured having a slightly inward projecting recess 92 formed in relation to the configuration of the lower portion of the camera lens 70 to provide means for supporting the camera lens 70 when housed therein. Alternatively, the second end 90 of the end piece 86 may be formed having a diameter slightly smaller than the diameter of the first end 88 of the end piece 86 to provide means for force-fitting the lower body portion of the camera lens 70 in relation thereto. In addition to the means of engagement outlined above, those skilled in the art will readily recognize other possible modifications and adaptations which are consistent with the spirit and scope of the present invention.

As disclosed, the lens cover 74 includes the upper housing member 76 and the end piece 86 operatively disposed in a rotatable relation therebetween. In operative structure, an interlocking ridge 84 is preferably formed adjacent the second end 82 of the housing member 76 which extends substantially therearound. Correspondingly, one or more fastener tabs 96 may be formed at a first end 88 of the end piece 86 which may engage the interlocking ridge 84 of the housing member 76 when disposed in engagement therewith. The fastener tabs 96 are preferably configured comprising a flexible extension member which preferably engages the ridge 84 of the housing member 76 in a snap-fit relationship when passed thereover. In this manner, a sterile surface is provided by means of the upper housing member 76 and the end piece 86, thus allowing a surgeon or surgical assistant to manually adjust the variable focus or zoom capability of the camera lens 70 being substantially disposed within the sterile lens cover 74.

Figure 6:
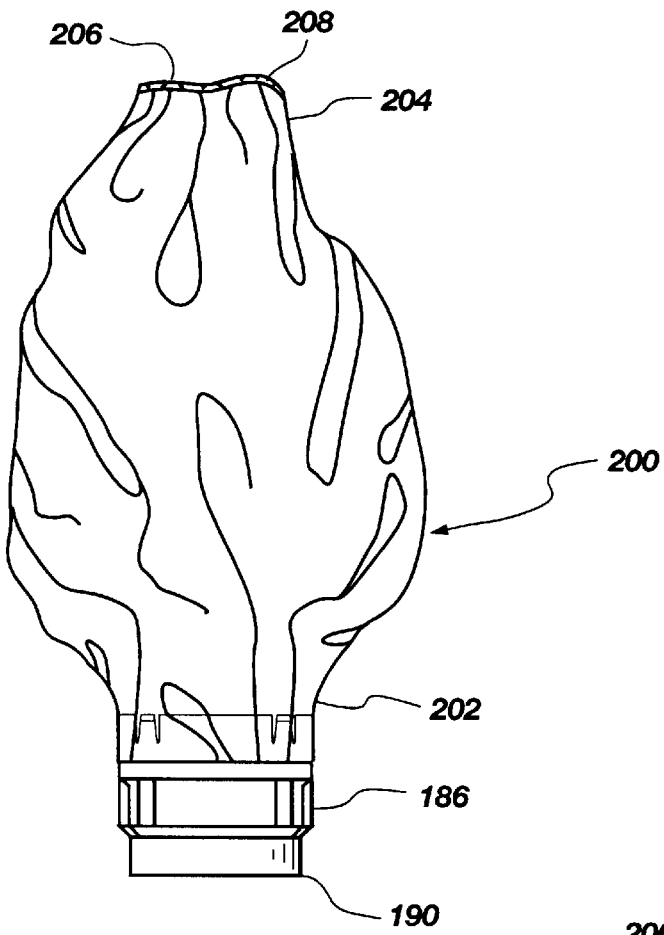
FIG. 6 is a perspective view of a sterile draping member of one presently preferred embodiment of the present invention being disposed in connection with an end piece of the housing assembly of one presently preferred embodiment of the present invention.
Figure 7:
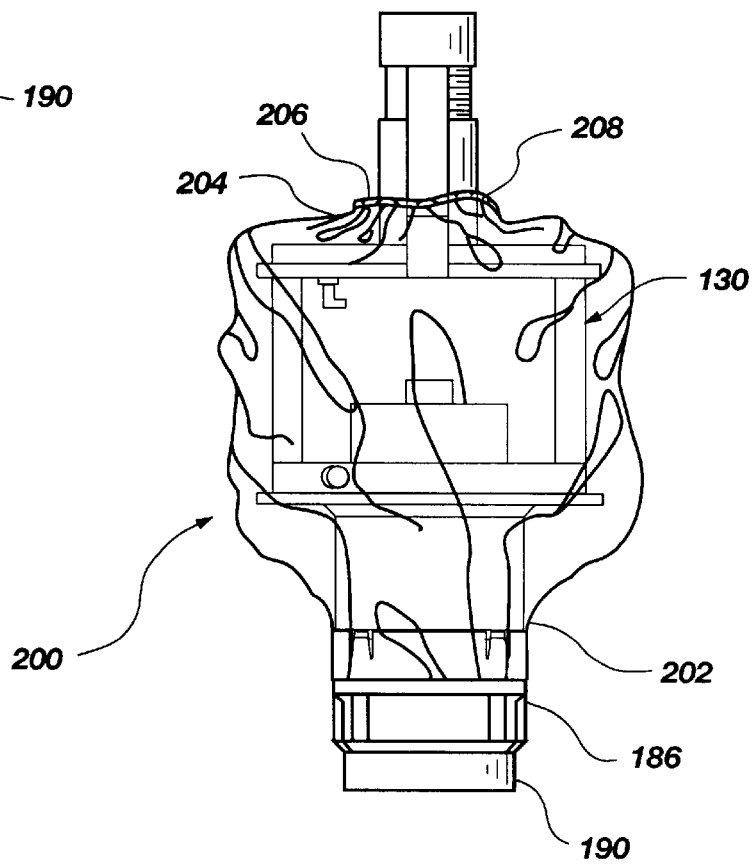
FIG. 7 is a perspective view of the sterile draping member of one presently preferred embodiment of the present invention draped over the housing member and the retaining assembly of one presently preferred embodiment of the present invention.

Referring now to FIGS. 6 and 7, an alternate preferred embodiment of an end piece 186 of the present invention is shown including a draping member 200. In construction, the draping member 200 is formed of a disposable material which is capable of being sterilized to provide a sterile surface over the surgical camera assembly 10. Correspondingly, the draping member 200 preferably is formed of a conventional polyethylene (homopolymer) plastic bag which is inherently clear in color to provide means for seeing the camera assembly 10 housed therein to allow for manually orienting the surgical camera assembly 10 and the light source 12 over the operative field.

Preferably, the draping member 200 comprises a first end 202, a second opposing end 204, and an intermediate body portion disposed therebetween. The first end 202 of the draping member 200 is preferably attached to the exterior surface of the end piece 186 substantially proximate the midsection or first end 90 thereof by means of a conventional fastening member. For example, the first end 202 of the draping member 200 may be fastened to the end piece 86 by an adhesive, a ring member having a configuration sufficient in dimension for being disposed against the ridge 93 formed in the midsection of the end piece 86 to provide means for restricting slippage therebetween, etc. It will be apparent to those skilled in the art that other fastening means or members may be constructed in accordance with the inventive principles set forth herein. It is intended, therefore, that the examples provided herein be viewed as exemplary of the principles of the present invention, and not as restrictive to a particular structure for implementing those principles.

Extending between the first and second ends 202, 204 of the draping member 200, the intermediate body portion is preferably formed having an internal periphery sufficient in size to substantially cover a portion of the surgical camera assembly 10, as best illustrated in FIG. 7. Additionally, the draping member 200 preferably comprises a closeable opening 206 which may incorporate a means for closing 208 the opening 206 formed at the second end 204 of the draping member 200. For example, a drawstring arrangement, elastic member, etc. disposed in relation to the closeable opening 206 may provide means for restricting the opening 206 of the draping member 200 around the first end 32 of the retaining assembly 30. It will be readily appreciated, however, that the means for closing 208 the opening 206 of the draping member 200 can, of course, be formed of a wide variety of other suitable materials or components.

In regards to the foregoing means for substantially covering the retaining assembly 30 of an alternate preferred embodiment of the present invention, the end piece 186 and the draping member 200 are preferably the only elements of the surgical camera assembly 10 which provide sterile surfaces for manually orienting the light source 12 and surgical camera assembly 10 over the operative field and for providing sterile surfaces for manually adjusting the variable focus and zoom capability of the camera lens 70.

In operation, the method of one presently preferred embodiment of the present invention provides for visually reproducing an operative field with enhanced focal illumination by means of disposing a surgical camera assembly 10 in operable engagement with a light source 12. Referring back to FIG. 1, the light source 12 is preferably supported adjacent or over the operative field by means of at least one articulating extension arm 18 extending from a support member 16 mounted at the ceiling 15 of an operating room. To prepare the light source 12 for engagement with the surgical camera assembly 10, the light source 12 may need to be adjusted for a downward drift caused by means of the association there between. Whereas, attaching the camera assembly 10 to the light source 12 may result in additional downward weight acting upon the articulating extension arms 18 of the support member 16 which may require adequate resistive compensation accordingly.

If the surgical camera assembly 10 is to be temporarily installed, the camera cable 68 may be extended along the vertical rise of the articulating extension arms 18 preferably supporting the light source 12 and directed horizontally until being sufficiently removed from the sterile operative field. Additionally, the camera cable 68 may be disposed in relation to an IV stand outside the sterile field and further disposed in connection with the remote camera controller 98. Similarly, if the surgical camera assembly 10 is to be permanently installed in the operating room, the camera cable 68 is preferably disposed along the horizontal and vertical rise of the articulating extension arms 18 and further suspended along the ceiling 15 where fixation devices may be used to attach the cable 68 in an appropriate direction to be further connected with the remote camera controller.

In one presently preferred embodiment, the camera assembly 10 preferably comprises a retaining assembly 30 formed of a sterilizable material and having a first end 32 removably disposed in engagement with the light source 12. In function, the retaining assembly 30 preferably provides a sterile surface for allowing a surgeon or surgical assistant to manually orient the light source 12 and surgical camera assembly 10 adjacent or over the operative field.

Engaging a second opposing end 38 of the retaining assembly 30 is a camera lens 70 which provides means for producing visual images of the operative field. In preferred structure, an adjustment member 58, such as, for example, a lever, screw, bolt, etc., may be operably disposed in a through-bore formed between the flange 33 and the first end 32 of the retaining assembly 30 to provide means for adjusting the rotation of the camera lens 70 in relation to the retaining assembly 30. As illustrated in FIG. 5, the camera lens 70 is substantially introduced and housed within a lens cover 74 (e.g., an end piece 86 rotatably engaging an upper housing member 76).

As generally explained above, to further maintain the sterility of the lens cover 74 of one presently preferred method of the present invention, a non-sterile member of the operating room staff preferably holds the upper portion of the elongated body of the camera lens 70, while a sterile operating room technician or surgical assistant carefully maneuvers the end piece 86 over the lower body portion of lens 70. By holding the sterile end piece 86 housing the lower body of the camera lens 70, the upper housing member 76 is operably disposed over the first end 72 and adjacent the upper portion of the elongated body of the camera lens 70. The sterile operating room technician or surgical assistants should be careful not to physical touch any part of the non-sterile camera lens (i.e., the lens thread, tabs and/or focus ring).

As disclosed above, the end piece 86 and the upper housing member 76 of the lens cover 74 comprises a rotatable engagement therebetween. After substantially housing the elongated body of the camera lens 70, a sterile operating room technician or surgical assistant may removably dispose the connecting member 72a of the lens 70 in relation to the camera head 60. Further, the first end 70 of the camera lens 70 may be disposed at the second end 38 of the retaining assembly 30 to provide an operable engagement therebetween.

When disposing the first end 72 of the camera lens 70 at the second end 38 of the retaining assembly 30, a fastener 52 is preferably removed from a corresponding through-bore 50 to provide means for disengaging a pivotal swing arm assembly 44 from a stationary member 42. In doing so, the alignment tabs 71 formed adjacent the first end 72 of the camera lens 70 are disposed in operable engagement with the alignment members 54 formed at the second end 38 of the retaining assembly 30. After the camera lens 70 is positioned in relation to the retaining assembly 30, the fastener 52 is introduced into the corresponding through-bore 50 to further engage the through-bore 48 formed in the stationary member 42, thus closing the orifice 40 at the second end 38 of the retaining assembly 30.

In operation, the lens cover 74 preferably provides a sterile surface for orienting the camera assembly 10 and/or for manually adjusting the variable focus and zoom capability of the camera lens 70. In an alternate preferred method of the present invention, the retaining assembly 30 and the upper housing member 76 of the lens cover 74 are not formed having a sterile surface. Consequently, an end piece 186 may be provided having a draping member 200 disposed in connection substantially proximate the midsection or first end 190 of the end piece 186. In this regard, an intermediate body portion of the sterile draping member 200 is draped over the non-sterile upper housing member and retaining assembly 130 in a conventional sterile fashion, thus providing a sterile surface for manually orienting the light source 12 and surgical camera assembly 10 over the operative field and for allowing for the manual adjustment of the variable focus and zoom capability of the camera lens 70.

Connected at a first end 72 of the camera lens 70 is a camera head 60. In function, the camera head 60 provides means for converting the visual images produced by the camera lens 70 into electrical signals which may be transmitted to a remote camera controller 98 for processing. The electrical signals are preferably transmitted from the camera head 60 to the remote camera controller 98 by means of an electrical camera cable 68. As will be readily appreciated by those skilled in the art, however, other conventional means of transmitting the electrical signals are contemplated by the spirit and scope of the present invention.

After the camera controller 98 has processed the electrical signals received from the camera head 60, the processed signals are preferably transmitted to a Video Cassette Recorder for recording. Moreover, a display 100 may be connected by means of an interactive cable 102 to the video cassette recorder to provide means for reproducing the visual images gathered by the camera lens 70 for observation on the display 100. In the preferred embodiment of the present invention, the surgical camera assembly 10 may include a means for recording sound (i.e., a microphone), thus providing a visual and audio reproduction of the surgical procedure. It will be readily understood by those skilled in the art that the visual images provided by the present invention are not limited to video, whereas still pictures and other types of media may be used.

From the above discussion, it will be appreciated that the present invention provides a surgical camera assembly operably disposed in connection with a light source to provide means for visually reproducing for demonstration a "bird's eye" view of an operative field with enhanced focal illumination and without disrupting the focal field of the surgical light by means of shadowing, whereby observers are provided with a clear and unobstructed view of the surgical procedure as it progresses. In this regard, it has been found that operating room technicians and surgical assistants who typically watch the display during an operative procedure are generally better able to anticipate the surgeon's needs, thereby reducing overall surgery time.

Unlike prior art devices, the surgical camera assembly of the present invention provides a sterile surface for orienting the light source and camera assembly in relation to the operative field which is capable of providing means for being universally interchangeable or adaptable to various lighting systems or surgical lamps found in the offices of physicians, clinical laboratories, research facilities, emergency rooms,dentist offices or the like. Similarly, the present invention provides a housing assembly or lens cover substantially housing the elongated body of a camera lens and providing a sterile surface for adjusting the variable focus and zoom capability of the camera lens to provide means for enhancing the visual images of the operative field. In this regard, the surgical camera assembly of the present invention preferably comprises a housing assembly adaptable for pre-sterilization and for packaging as a disposable product, thus being generally cost effective in light of mass production and readily available for emergency procedure.

Consistent with the foregoing advantages, the surgical camera assembly is capable of increasing or decreasing the magnification of the images produced by the camera lens without having to physically move the light source closer or farther away from the operative field. Moreover, the present invention is readily adaptable as an enhancement to existing equipment or systems, whereby avoiding the costs of installation associated with hard-wiring a dedicated camera to a single light source.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A surgical camera assembly operatively disposed in connection with a light source to provide means for visually producing for demonstration an operative field with enhanced focal illumination, said camera assembly comprising:

a support structure for supporting said light source adjacent said operative field;

a retaining assembly comprising a first end, a second opposing end, and at least one gripping member, said first end of said retaining assembly removably engaging said light source, said second end of the retaining assembly forming a closeable opening;

an optical lens for producing visual images of said operative field, said optical lens having a first end, an elongated body, a variable focus and zoom capability, and means for adjusting said focus and zoom capability, said first end of said optical lens adapted for engaging said second end of said retaining assembly;

a housing assembly including a first end and an elongated channel extending from said first end, said channel having an internal periphery sufficient for housing said elongated body of said optical lens therein, said housing assembly providing a sterile surface for manipulating said means for adjusting said focus and zoom capability of the optical lens; and a camera head for converting said visual images provided by said optical lens into electrical signals, said camera head including a first end and a second opposing end, said first end disposed between said first and second ends of said retaining assembly, said second end disposed in connection with said first end of said optical lens providing an operational engagement therebetween.

2. A surgical camera assembly as defined in claim 1 wherein said light source provides high intensity light.

3. A surgical camera assembly as defined in claim 1 wherein said support structure comprises at least one articulating extension arm connected to said light source.

4. A surgical camera assembly as defined in claim 3 wherein said articulating extension arm provides means for moving said light source in relation to said support structure.

5. A surgical camera assembly as defined in claim 1 wherein said support structure includes means for portability.

6. A surgical camera assembly as defined in claim 1 wherein said retaining assembly provides a sterile surface for orientation of said light source and said optical lens.

7. A surgical camera assembly as defined in claim 1 wherein said first end of said retaining assembly comprises means for shielding a hand of an operator from contacting said light source proximate said retaining assembly.

8. A surgical camera assembly as defined in claim 7 wherein said shielding means comprises a flange extending radially outward from said first end of said retaining assembly.

9. A surgical camera assembly as defined in claim 1 wherein said second end of said retaining assembly comprises a stationary member and a pivotal swing arm assembly, said stationary member and said pivotal swing arm assembly, in combination, providing means for closing said closeable opening.

10. A surgical camera assembly as defined in claim 1 wherein said second end of said retaining assembly comprising at least one alignment member removably engaging said first end of said optical lens.

11. A surgical camera assembly as defined in claim 1 wherein said first end of said optical lens comprising at least one alignment tab providing means for engaging said second end of said retaining assembly.

12. A surgical camera assembly as defined in claim 1 wherein said housing assembly comprises an upper housing member and an end piece.

13. A surgical camera assembly as defined in claim 12 wherein said housing member being removably disposed over an upper portion of said elongated body of said optical lens and comprising an interlocking ridge.

14. A surgical camera assembly as defined in claim 12 wherein said end piece being removably disposed over a lower portion of said elongated body of said optical lens, said end piece further comprising means for engaging said housing member in rotatable relation thereto.

15. A surgical camera assembly as defined in claim 1 wherein said housing member comprises a draping member engaging said first end of said housing member and being removably disposed over said retaining assembly, said draping member providing a sterile surface for orienting said retaining assembly and said optical lens in relation to said operative field.

16. A surgical camera assembly as defined in claim 15 wherein said draping member having a first end and an enlarged opening disposed at said first end, said opening comprising means for substantially closing said opening at said first end of said retaining assembly.

17. A surgical camera assembly as defined in claim 1 further comprising a remote camera controller for gathering and processing said electrical signals produced by said camera head.

18. A surgical camera assembly as defined in claim 17 further comprising an electrical cable extending between said camera head and said remote camera controller for transmitting said electrical signals from the camera head to the remote camera controller.

19. A surgical camera assembly as defined in claim 18, wherein said retaining assembly comprises an elongated slot formed in said first end for retaining a portion of said electrical cable.

20. A surgical camera assembly as defined in claim 17 further comprising a display monitor comprising means for receiving said electrical signals processed by said remote camera controller and for displaying said visual images produced by said optical lens.

21. A surgical camera assembly operatively disposed in connection with a light source to provide means for visually producing for demonstration an operative field with enhanced focal illumination, said camera assembly comprising:

a support structure for supporting said light source adjacent said operative field;

a retaining assembly comprising a first end, a second opposing end, and at least one gripping member, said first end of said retaining assembly removably engaging said light source and comprising means for shielding a hand of an operator from contact with said light source proximate said retaining assembly, said second end of the retaining assembly forming a closeable opening and including at least one alignment member;

an optical lens for producing visual images of said operative field, said optical lens having a first end, an elongated body, a variable focus and zoom capability, and means for adjusting said focus and zoom capability, said first end of said optical lens adapted for removably engaging said second end of said retaining assembly by means of at least one alignment tab operably disposed in relation to said alignment member of said retaining assembly;

a housing assembly including a first end and an elongated channel extending from said first end, said channel having an internal periphery sufficient for removably housing said elongated body of said optical lens therein, said housing member providing a sterile surface for manually manipulating said means for adjusting said focus and zoom capability of the optical lens;

a video camera head for converting said visual images provided by said optical lens into electrical signals, said camera head including a first end and a second opposing end, said first end removably disposed between said first and second ends of said retaining assembly, said second end disposed in connection with said first end of said optical lens providing an operational engagement therebetween;

a remote camera controller for gathering and processing said electrical signals produced by said camera head;

an electrical cable extending between said camera head and said remote camera controller for transmitting said electrical signals from the camera head to the remote camera controller; and a display monitor comprising means for receiving said electrical signals processed by said remote camera controller and for displaying said visual images produced by said optical lens.

22. A surgical camera assembly as defined in claim 21 wherein said light source provides high intensity light.

23. A surgical camera assembly as defined in claim 21 wherein said support structure comprises at least one articulating extension arm connected to said light source.

24. A surgical camera assembly as defined in claim 23 wherein said articulating extension arm provides means for moving said light source horizontally in relation to said support structure.

25. A surgical camera assembly as defined in claim 23 wherein said articulating extension arm provides means for moving said light source vertically in relation to said support structure.

26. A surgical camera assembly as defined in claim 21 wherein said support structure includes means for portability.

27. A surgical camera assembly as defined in claim 21 wherein said retaining assembly provides a sterile surface for orientation of said light source and said optical lens.

28. A surgical camera assembly as defined in claim 21 wherein said retaining assembly comprises an elongated slot formed in said first end for retaining a portion of said electrical cable.

29. A surgical camera assembly as defined in claim 21 wherein said second end of said retaining assembly comprises a stationary member and a pivotal swing arm assembly, said stationary member and said pivotal swing arm assembly, in combination, providing means for closing said closeable opening.

30. A surgical camera assembly as defined in claim 21 wherein said housing assembly comprises a housing member and an end piece.

31. A surgical camera assembly as defined in claim 30 wherein said housing member being removably disposed over an upper portion of said elongated body of said optical lens and comprising an interlocking ridge.

32. A surgical camera assembly as defined in claim 30 wherein said end piece being removably disposed over a lower portion of said elongated body of said optical lens, said end piece further comprising means for engaging said housing member in rotatable relation thereto.

33. A surgical camera assembly as defined in claim 21 wherein said housing member comprises a draping member engaging said first end of said housing assembly and being removably disposed over said retaining assembly, said draping member providing a sterile surface for orienting said retaining assembly and said optical lens in relation to said operative field.

34. A surgical camera assembly as defined in claim 33 wherein said draping member having a first end and an enlarged opening disposed at said first end, said opening comprising means for substantially closing said opening at said first end of said retaining assembly.

35. A method for visually producing an operative field with enhanced focal illumination using a sterile camera assembly, said method comprising the steps of:
   supporting a light source adjacent said operative field, said light source disposed in connection with a support structure;
   mounting a retaining assembly to said light source;
   providing an optical lens for producing visual images of said operative field, said optical lens having a first end, an elongated body, and variable focus and zoom capability;
   introducing said elongated body of said optical lens within a housing assembly, said housing assembly having a first end and providing a sterile surface for manually adjusting said focus and zoom capability of said optical lens;
   disposing said first end of said optical lens in operable engagement with said retaining assembly;
   connecting a camera head to said optical lens, said camera head providing means for converting said visual images produced by said optical lens into electrical signals;
   transmitting said electrical signals to a remote camera controller for processing;
   converting said processed electrical signals into said visual images; and
   displaying said visual images on a display.

36. A method as defined in claim 35 further comprising the step of engaging at least one alignment tab formed at said first end of said optical lens with at least one alignment member of said retaining member.

37. A method as defined in claim 35 wherein said housing assembly further comprises a housing member engaging an end piece, wherein manually adjusting said variable focus and zoom capability of said optical lens includes rotating said end piece in relation to said housing member.

38. A method as defined in claim 35 wherein said retaining assembly further comprises a sterile exterior surface for manually positioning said light source and said optical lens in relation to said operative field.

39. A method as defined in claim 35 wherein said housing assembly further comprises a draping member engaging said first end of said housing assembly and being removably disposed over said retaining assembly to provide a sterile surface for manually positioning said light source and said optical lens in relation to said operative field.

* * * * *